United States Patent [19]
Geks et al.

[11] 3,950,509
[45] Apr. 13, 1976

[54] METHOD OF CONTROLLING PERSPIRATION ODOR WITH A BIOLOGICAL PROTEASE INHIBITOR

[75] Inventors: Franz-Josef Geks, Cologne; Gunter Schmidt-Kastner, Wuppertal-Elberfeld, both of Germany

[73] Assignee: Bayer Aktiengesellschaft, Leverkusen, Germany

[22] Filed: Feb. 20, 1974

[21] Appl. No.: 444,164

Related U.S. Application Data

[63] Continuation of Ser. No. 280,151, Aug. 14, 1972, abandoned, and a continuation of Ser. No. 242,218, April 17, 1972, and a continuation-in-part of Ser. No. 59,339, July 29, 1970, abandoned.

[30] Foreign Application Priority Data

Aug. 2, 1969  Germany............................ 1939419

[52] U.S. Cl. ............. 424/65; 252/107; 424/DIG. 5; 424/47; 424/168
[51] Int. Cl.².......................................... A61K 7/32
[58] Field of Search .................. 424/65, 94; 167/65; 252/106, 107

[56] References Cited
UNITED STATES PATENTS

| | | | |
|---|---|---|---|
| 2,431,119 | 11/1947 | Horvath........................... | 424/177 X |
| 3,071,510 | 1/1963 | Wershaw et al..................... | 424/177 |
| 3,181,997 | 5/1965 | Schultz ................................. | 424/94 |
| 3,558,773 | 1/1971 | Schultz .............................. | 424/177 |

FOREIGN PATENTS OR APPLICATIONS

| | | | |
|---|---|---|---|
| 1,155,563 | 10/1963 | Germany ............................ | 424/177 |
| 1,241,153 | 7/1960 | France............................... | 424/177 |
| 7,010,797 | 2/1971 | Germany ............................. | 424/65 |

OTHER PUBLICATIONS

Brevet Special De Medicament–BSM4198M, (France) 7/1966.

*Primary Examiner*—Dale R. Ore
*Attorney, Agent, or Firm*—Depaoli & O'Brien

[57] ABSTRACT

A method of reducing body odor by applying to the body an aqueous odor-reducing composition containing a perspiration odor-reducing or retarding amount of a biological protease-inhibitor.

1 Claim, No Drawings

METHOD OF CONTROLLING PERSPIRATION ODOR WITH A BIOLOGICAL PROTEASE INHIBITOR

BACKGROUND OF THE INVENTION

This is a continuation of application Ser. No. 280,151, filed Aug. 14, 1972, now abandoned.

The present application is a continuation-in-part of copending application Ser. No. 59,339, filed July 29, 1970, now abandoned, in favor of a continuation application Ser. No. 242,218, filed Apr. 7, 1972.

FIELD OF THE INVENTION

The present invention relates to, in general, topical deodorant compositions and, in particular, to deodorant compositions to be applied to the skin. More particularly, the invention is directed to novel, topical deodorant compositions containing, as an active perspiration odor reducer or retarder, an effective amount of a biological protease-inhibitor.

Description of the Prior Art

Perspiration, or sweat, is the clear liquid exuded from or excreted by the sudoriparous glands. It possesses a characteristic odor, and a salty taste; its reaction is normally alkaline, but, when mixed with sebum, it is acid. It contains sodium chloride, cholesterin, fats, and fatty acids and traces of albumin, urea, and other compounds.

The perspiration or sweat, in combination with skin bacteria, provide a suitable medium for the elaboration and production of biological proteases or proteolytic enzymes further contributing to the odor caused by perspiration.

Cosmetic preparations whish have a perspiration odor-reducing or retarding effect are well-known. Many substances of different chemical compositions have, heretofore, been suggested for use as materials capable of reducing or retarding the odor of perspiration. Among such substances may be mentioned, for example, 2,2'-methylene-bis-(3,4,6-trichlorophenol), chlorinated diphenyl ureas, such as, 3,4,4'-trichlorocarbanilide, 1.6di-4-chlorophenyl-diquanidohexane, hydroxy benzoic acid methyl ester, halogenated phenols, such as, bis-(hydroxy-3,5-dichlorophenyl) sulphide, as well as other bacteriostatic materials, such as, for example, antibiotics.

Many of the aforementioned substances, however, exhibit characteristics which detract from their value as deodorants and militate against their extended use because they are not well tolerated by the human body and induce undesirable side effects, such as, skin irritation, eczema allergies, and the like. Additionally, many of such substances of the prior art have the disadvantage of forming strong acid solutions which can cause damage to clothing and delicate fabrics.

DESCRIPTION OF THE INVENTION

The present invention contemplates improved topical compositions of matter containing biological protease-inhibitors which, when applid to the living skin, effectively reduce or retard the odor caused by perspiration.

The biological protease-inhibitors which find utility in the manufacture of the improved topical compositions of the invention as deodorants include protease-inhibitors as, for example, kallikrein-trypsin-inhibitors from pancreas, liver, lung, lymph glands, parotid glands, spleen and blood serum and protease-inhibitors of vegetable origin, for example the inhibitors from potatoes [A. K. Balls, C. A. Ryan, J. Biological Chem. 238, 2976 (1963)] and leguminous plants.

Biological protease-inhibitors, such as kallikrein-inhibitors, are readily available by the methods and procedures described, for example, in U.S. Pat. No. 3,181,997 and U.S. Pat. No. 3,558,773.

In the compositions of the invention, the concentration of the biological protease-inhibitor is not necessarily a critical feature of the invention and can be varied over a wide range. It has been found, however, that 0.1 to 5.0 weight percent solutions of the biological protease-inhibitors incorporated into the deodorant compositions provide compositions suitable as deodorants with immediate and lasting effects. Particularly suitable compositions comprise aqueous solutions containing from about 0.1 to 1.0 weight percent of the biological protease-inhibitor. Such solutions will provide at least a concentration on the skin area, for deodorizing purposes, of 0.1 ml. per $cm^2$. As the compositions of the invention are amenable for use in forms other than aqueous solutions, such as, creams, ointments, lotions, aerosol sprays, stick pencils, soaps, and the like, similar dosages or concentrations of the biological protease-inhibitors therein are to be observed. In preparing such formulations, standard manufacturing processes can be employed. Typical processes for formulating various cosmetic preparations are illustrated in Chemie-Lexikon, 6th Edition, Vol. 1, Col. 1402 and 1403 (H. Rompp).

It is to be understood that the biological protease-inhibitors can be used alone or in combinations with one another to obtain, in some cases, a synergistic effect. Also, it is to be understood that other ingredients can be incorporated into the compositions to obtain a product having properties from a purely cosmetic aspect. Further, if desired, various bacteriostatic and germicidal agents may be added to the compositions of the invention. The use of such additives is optional and, while contemplated in the commercial practice of the invention, their presence is not essential to the deodorizing function of the compositions of the invention.

The efficacy of the various compositions of the invention as deodorants was demonstrated in many series of experiments and demonstrated that they possessed strong deodorizing action without undesirable side effects. In a typical experiment, a swatch of cloth moistened with a solution containing 1.5 weight percent of a biological protease-inhibitor, such as, kallikrein-inhibitor, was placed in one armpit and a comparable swatch moistened with distilled water was placed in the other armpit overnight. Upon subsequent examination and observation, it was found that the swatch moistened with the aqueous solution containing the biological protease-inhibitor remained completely odorless, while the swatch of cloth moistened with distilled water possessed a distinct odor of sweat.

The following examples will serve to illustrate the various forms in which the invention can be utilized and the utility thereof in maintaining and/or enhancing the odor reducing or retarding effects of the compositions when applied to the living body in the sweat producing areas, such as the armpits of a person.

EXAMPLE 1

A small piece of cloth was immersed into an aqueous solution containing 1.5 weight percent of kallikrein-trypsin inhibitor and the cloth, thus dampened, was placed into the armpit of a human test subject and, by way of comparison, an equivalent piece of cloth, dampened with distilled water, was placed into the opposite armpit and both pieces left overnight.

Prior to placing both pieces of dampened cloth into their respective armpits, they are examined visually and sniffed for odor and found to be visually identical and odorless. Subsequently, both pieces were removed and examined visually and tested for odor. The piece of cloth that had been dampened with an aqueous solution of kallikrein-trypsin inhibitor was odorless while the piece of cloth dampened with distilled water had a definite odor of sweat when sniffed to detect same.

EXAMPLE 2

An emulsified base for a deodorant body cream is prepared comprising the following ingredients:
a. 60 grams of a non-organic emulsifier;
b. 70 grams of paraffin oil;
c. 50 grams of neutral oil;
d. 10 grams of Purcellin liquid; and
e. 310 grams of water.

The above ingredients are mixed and emulsified at a temperature of 70°C. and the resultant emulsion cooled to a temperature of 45°C. Subsequently, the emulsion is combined with a solution of the biological protease inhibitor isolated from potatoes and 400 grams of water and the entire mass further emulsified to form a deodorant cream mixture.

Application of the deodorant cream mixture to the armpits of human subjects in a manner similar to Example 1, above, provides similar results.

Similar results are also obtained by substituting in the above formulation the kallikrein-trypsin inhibitor for the biological protease inhibitor derived from potatoes.

EXAMPLE 3

A deodorant soap is prepared, in accordance with the invention, by mixing together 1000 grams of flakes of soap having a palm nut fatty acids-coconut fatty acids base and 30 grams of pelletized biological protease inhibitor derived from potatoes. After thorough mixing, the mixture is divided and pressed into cakes of soap.

Washing and bathing by human subjects with the deodorant cakes of soaps prepared above provides results similar to those of Example 1.

Similar results are also obtained by substituting in the above formulation the kallikrein-trypsin inhibitor for the biological protease inhibitor derived from potatoes.

EXAMPLE 4

A deodorant stick or pencil is prepared by heating together at a temperature of 80°C.:
a. 500 grams of propylene glycol; and
b. 125 grams of Isonon liquid 70%. The mixture is allowed to cool to a temperature of 45°C. and combined with a solution of 20 grams of the biological protease inhibitor derived from potatoes in 285 grams of water. The resultant mixture is cast into forms of pencil bodies and cooled.

Subsequent application of the deodorant pencil sticks prepared above to the armpits of human subjects provides results similar to those observed in Example 1.

Similar results are also obtained by substituting in the above formulation the kallikrein-trypsin inhibitor for the biological protease inhibitor derived from potatoes.

While the invention has been described in detail above, it is apparent that it is capable of numerous modifications and embodiments without departing from the essential spirit and character thereof. Thus, the scope of the invention is not intended to be limited by the specific disclosure above but only as defined by the subjoined claims.

What is claimed is:

1. The method of controlling perspiration odor which comprises topically applying to the human skin a deodorant composition containing in an effective perspiration odor-reducing amount between 0.1 to 5.0 weight percent of a biological protease inhibitor selected from the group consisting of kallikrein-trypsin inhibitor from the pancreas liver, lung, lymph glands, parotid glands, spleen, or blood serum and biological vegetable protease inhibitor derived from potatoes in a cosmetic carrier.

* * * * *

UNITED STATES PATENT OFFICE
CERTIFICATE OF CORRECTION

Patent No. 3,950,509  Dated April 13, 1976

Inventor(s) Franz-Josef Geks et al

It is certified that error appears in the above-identified patent and that said Letters Patent are hereby corrected as shown below:

Column 1, line 36, "whish" should be --which--.

Column 1, line 46, "(hydroxy-3...)" should be --(2-hydroxy-3...)--

Signed and Sealed this

Seventh Day of September 1976

[SEAL]

Attest:

RUTH C. MASON
*Attesting Officer*

C. MARSHALL DANN
*Commissioner of Patents and Trademarks*